United States Patent [19] [11] 4,279,777
Velenyi et al. [45] Jul. 21, 1981

[54] MOLYBDENUM-COPPER-TIN CATALYSTS

[75] Inventors: Louis J. Velenyi, Lyndhurst; Andrew S. Krupa, Twinsburg, both of Ohio

[73] Assignee: The Standard Oil Company, Cleveland, Ohio

[21] Appl. No.: 102,087

[22] Filed: Dec. 10, 1979

[51] Int. Cl.³ .................. B01J 27/02; B01J 27/14; B01J 23/10; B01J 23/14
[52] U.S. Cl. .................. 252/439; 252/435; 252/437; 252/462; 252/464; 252/465; 585/445
[58] Field of Search ........... 252/435, 437, 439, 462, 252/464, 465

[56] References Cited

U.S. PATENT DOCUMENTS

| 3,801,670 | 4/1974 | Shiraishi et al. | 252/464 X |
| 3,951,861 | 4/1976 | Shiraishi et al. | 252/464 X |
| 3,956,377 | 5/1976 | Dolhyj et al. | 252/462 X |
| 3,988,359 | 10/1976 | Saito et al. | 252/439 X |
| 4,017,423 | 4/1977 | White et al. | 252/437 |
| 4,123,388 | 10/1978 | Kerr et al. | 252/435 X |
| 4,148,757 | 4/1979 | Brazdil | 252/465 X |
| 4,163,862 | 8/1979 | Dolhyj et al. | 252/462 X |
| 4,174,459 | 11/1979 | Sakamoto et al. | 252/435 X |

Primary Examiner—Delbert E. Gantz
Assistant Examiner—William G. Wright
Attorney, Agent, or Firm—Gary R. Plotecher; Herbert D. Knudsen; Larry W. Evans

[57] ABSTRACT

Dehydrogenatable hydrocarbons are dehydrogenated by contacting them at dehydrogenation conditions in the presence of a complex oxide catalyst comprising molybdenum, copper and tin and at least one element selected from the group consisting of Li, Na, K, Rb, Cs, Mg, Ca, Sr, Ba, La, Ce, Th and U. For example, an alkyl aromatic hydrocarbon, e.g. ethylbenzene, can be dehydrogenated to an alkenyl aromatic hydrocarbon, e.g. styrene, in the presence of an oxide complex catalyst comprising molybdenum, copper, tin and at least one element selected from the group consisting of K, Cs, Ba, Mg and Ca.

9 Claims, No Drawings

MOLYBDENUM-COPPER-TIN CATALYSTS

BACKGROUND OF THE INVENTION

This invention relates to both a novel catalyst and a dehydrogenation process using this novel catalyst. The catalyst comprises an oxide complex of molybdenum, copper, tin and a promoter metal. The process comprises dehydrogenating a dehydrogenatable hydrocarbon in the presence of this catalyst to produce a hydrocarbon product containing the same number of carbon atoms but fewer hydrogen atoms.

The dehydrogenation of organic compounds for the production of compounds having a higher degree of unsaturation is generally well known. This process can be illustrated by the following general equation:

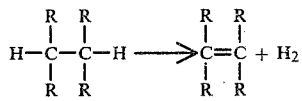

wherein R is a suitable substituent.

Organic compounds are commercially dehydrogenated by contacting the compound to be dehydrogenated at an elevated temperature, preferably in the presence of a catalyst. However, according to many of these prior art processes, the products are obtained at relatively low levels of conversion and selectivity. The instant process achieves high selectivities and conversions through the use of a special catalyst comprising a promoted oxide complex of molybdenum, copper and tin.

SUMMARY OF THE INVENTION

The present invention provides an improvement in the catalyst used for dehydrogenation reactions. Specifically, this invention provides a catalyst comprising an oxide complex of molybdenum, copper, tin and at least one promoter element selected from the group consisting of Li, Na, K, Rb, Cs, Mg, Ca, Sr, Ba, La, Ce, Th and U. Moreover, the present invention provides a process wherein dehydrogenatable hydrocarbons are dehydrogenated by contacting the hydrocarbons with the inventive catalyst.

More specifically, the present invention provides an oxide complex catalyst comprising molybdenum, copper, tin and at least one promoter element selected from the group consisting of K, Cs, Ba, Mg and Ca and the use of this catalyst in the process for producing an alkenyl aromatic hydrocarbon by dehydrogenating an alkyl aromatic hydrocarbon.

DETAILED DESCRIPTION

Reactants

The dehydrogenatable hydrocarbon that is subjected to the method of this invention can, in general, be an organic compound having 2 to 30 carbon atoms per molecule and containing at least one pair of adjacent carbon atoms each having hydrogen attached thereto. More particularly, suitable dehydrogenatable hydrocarbons are aliphatic compounds containing 2 to 30 carbon atoms per molecule, alkyl aromatic hydrocarbons where the alkyl group contains 2 to 6 carbon atoms, and naphthenes or alkyl substituted naphthenes.

Specific examples of suitable hydrocarbons are (1) alkanes such as ethane, propane, n-butane, isobutane, n-pentane, isopentane, n-hexane and 2-methylhexane; (2) naphthenes such as cyclopentane, cyclohexane and methylcyclohexane; and (3) alkyl aromatics such as ethylbenzene, n-butylbenzene, 1,3,5-triethylbenzene, n-propylbenzene, isobutylbenzene, ethylnaphthalene, cumene, ethylpyridine, 1,1-diphenylethane and 1,2-diphenylethane.

Any material which is inert to the reactants, catalysts and products of this reaction may also be included in the reaction system as a diluent. For example, steam, nitrogen gas, inert gases, carbon dioxide, paraffins and/or benzene can be added to the reaction system, if desired.

Process Conditions

In carrying out the inventive process, the dehydrogenatable hydrocarbon is contacted with a catalyst as described below for effecting the dehydrogenation process. This reaction can be accomplished both in the batch mode and continuously with both fixed and fluid catalyst beds.

Reaction temperatures are normally maintained at about 300° C. to 700° C., and more preferably 475° C. to 625° C. The reaction pressure is normally maintained at atmospheric pressure, but may also be conducted at subatmospheric or superatmospheric pressure. The apparent contact time between the catalyst and the reactants may vary from about 0.1 to 20 seconds for the fixed-bed process, and more preferably 1 to 10 seconds. In general, lower reaction temperatures require longer contact times and higher reaction temperatures require shorter contact times.

Catalysts

The catalyst employed in this invention comprises promoted molybdenum-copper-tin oxide complexes. These catalysts can be described by the formula:

wherein
A is at least one element selected from the group consisting of Li, Na, K, Rb, Cs, Mg, Ca, Sr, Ba, La, Ce, Th, U and mixtures thereof;
L is at least one element selected from the group consisting of Zn, Cd, Hg, Al, Ga, In, Tl, Ti, Zr, Hf, V, Nb, Ta, Ag, Au, Te, Se, Bi, Sb, Cr, W, As, P, S, Re, Mn, Group VIII elements and mixtures thereof; and
wherein
a is about 0.1–15;
b is about 0.1–15;
c is about 0.05–12;
d is about 0.01–10;
e is about 0–12; and
x is the number of oxygens sufficient to satisfy the valence requirements of the other elements present.

The catalyst may be any catalyst delineated by the general formula above with respect to the components of the catalyst. Preferred catalysts are those wherein A is at least one of K, Cs, Ba, Mg and Ca and wherein L is at least one of Bi, Te and Re. The ratio of the elements in the instant catalyst composition is important. In this regard, the preferred ratio of elements is as follows:
a is about 5;
b is about 3–8;
c is about 0.5–10;
d is about 0.5–10; and
e is about 0.5–6.

More preferably,
a is 5;
b is 4;
c is 0.05–5;
d is 1–5; and
e is 2.5–5.

This catalyst is also very effective when there are no L elements present. Moreover, preferred catalysts do not contain catalytic amounts of Group VIII elements, antimony or vanadium. Finally, it has even been discovered that the catalysts of this invention are effective in the absence of bismuth.

The exact chemical nature of the catalysts of this invention is not known. The catalyst may be a mixture of oxides, for example, or an oxide complex of all the contained elements. In any event, these catalysts are generally known in the art.

The catalysts of this invention can be made by techniques which are essentially the same as those techniques described in the art for other oxidation catalysts (see U.S. Pat. No. 3,642,930, which is herein incorporated by reference). Even though there are numerous preparations that may be utilized to give acceptable catalysts, some of the preferred methods of making the catalysts are described below.

The catalysts of the present invention can be prepared from any mixture of compounds that can be calcined to give the desired oxide component. Preferably the catalysts are prepared by coprecipitating decomposable salts such as nitrates, acetates, halides and/or oxides to form a catalyst precursor, and then calcining the precursor in the presence of oxygen. Other known catalyst preparation techniques, however, can be employed.

The catalytic activity of the catalysts embodied in the present invention is enhanced by heating the catalyst at elevated temperatures. Preferably, the catalysts are dried and heated at a temperature of about 260° C. to 1,000° C., more preferably at about 425° C. to 700° C., for from 2 to 24 hours. If the activity/selectivity relationship is not satisfactory, the catalyst can be further heat treated at a temperature above about 425° C. but below a temperature deleterious to the catalysts, preferably in the range from about 425° C. to about 800° C., for from 1 to 48 hours.

The catalyst, if desired, can be supported on a suitable support. Any known support material can be used which is stable under the reaction conditions to be encountered in the use of the catalyst and inert to the reaction system.

The dehydrogenation of dehydrogenatable hydrocarbons is an important chemical process because of the great and expanding demand for dehydrogenated hydrocarbons for use in the manufacture of various chemical products such as detergents, plastics, synthetic rubber, pharmaceutical products, high octane gasolines, perfumes, drying oils and various other products well known to those skilled in the art.

SPECIFIC EMBODIMENTS

In order to more thoroughly describe the present invention, the following working examples are presented. In each of these examples, ethylbenzene was dehydrogenated to styrene in a fixed-bed reactor.

The terms in the examples were defined as follows:

$$\% \ PPC = \frac{\text{Moles Carb. in Ethylbenzene Conv. to Prod.}}{\text{Moles Carb. in Ethylbenzene Fed}} \times 100$$

-continued
$$\% \ \text{Select.} = \frac{\text{Moles Carb. in Ethylbenzene Conv. to Prod.}}{\text{Moles Carb. in Ethylbenzene Reacted}} \times 100$$

The results have all been adjusted to a 100% carbon balance.

COMPARATIVE EXAMPLE A

A catalyst comprising 30% by weight $Mo_5Cu_4Sn_1O_x$, 52.5% by weight $SiO_2$ and 17.5% by weight $Al_2O_3$ was prepared by the following procedure. First, 15.97 gms. of copper acetate were dissolved in 800 ml. of distilled water. Next, 17.5 gms. of ammonium heptamolybdate were added and the resultant solution was brought to a boil. 3.01 gms. of tin dioxide were added and the solution was boiled for ½ hour and then 114.5 gms. of colloidal $SiO_2$ (Nalco 41DO1—41% silica by weight) and 15.65 gms. of Dispal, i.e. fine powder, alumina were added. The liquid was evaporated to a thick, light green paste and then dried for 4 hours at 110° C. The resultant green material was calcined at 380° C. for 2 hours in a muffle furnace.

17.5 cc. of this catalyst were placed in a fixed-bed reactor. 2.5 cc. Alundum on top of the catalyst served as an evaporation zone. The gaseous diluent, $N_2$, was introduced via a calibrated rotometer and the liquid feed, ethylbenzene, was supplied directly into the reactor using a Sage syringe pump. The reactor was heated in a stainless steel block to give the desired reaction temperature.

The off-gas was passed through a cold acetone scrubber where the liquid products were retained. These liquid products were then quantitatively analyzed using an H-P gas chromatograph. The tail gas was analyzed for $N_2$, CO and $CO_2$ using a Carle gas chromatograph. The results are shown in Table I.

EXAMPLE 1

A catalyst comprising 30% by weight $Mo_5Cu_4Sn_1Ba_1O_x$, 52.5% by weight $SiO_2$ and 17.5% by weight $Al_2O_3$ was prepared by the following procedure. First, 15.97 gms. of copper acetate were dissolved in 800 ml. of distilled water. 17.5 gms. of ammonium heptamolybdate were added to this solution and the resultant mixture was brought to a boil. Next, 3.01 gms. of tin dioxide were added and the solution was then boiled for ½ hour. 5.109 gms. of barium acetate were dissolved in 50 ml. of distilled water and then added to the solution prepared above. After boiling for 15 minutes, 114.5 gms. of colloidal $SiO_2$ (Nalco 41DO1) and 15.65 gms. of Dispal alumina were added. The liquid was evaporated to a light green paste and then dried for 4 hours at 110° C. The resultant hard green material was calcined at 380° C. for 2 hours in a muffle furnace.

The catalyst prepared by this procedure was placed into the apparatus described in Comparative Example A and the results are shown in Table I.

EXAMPLE 2

A catalyst comprising 30% by weight $Mo_5Cu_4Sn_1Bi_1Ba_1O_x$, 52.5% by weight $SiO_2$ and 17.5% by weight $Al_2O_3$ was prepared in the same way as Example 1 except that 3.11 gms. of $Bi_2O_3$ were added after the tin dioxide. This solution was boiled for ½ hour prior to the addition of the barium acetate.

This catalyst was placed in the apparatus described in Comparative Example A and the results are shown in Table I.

EXAMPLES 3 thru 9

Various other catalysts were prepared by the techniques disclosed in the above examples and placed into the experimental apparatus disclosed in Comparative Example A. The identity of these catalysts and the results of these experiments are shown in Table I.

TABLE I

Dehydrogenation of Ethylbenzene to Styrene

Pressure: Atmospheric
Catalyst: 30% $Mo_5Cu_4Sn_1$(promoter)$O_x$, 52.5% $SiO_2$, 17.5% $Al_2O_3$

| Example | Promoter | Temp (°C.) | Contact Time (Seconds) | Ethylbenzene Flow Rate (g Carb/Min) | Per Pass Conversion (% Styrene) | Selectivity (%) |
|---|---|---|---|---|---|---|
| A | — | 500 | 7.7 | 0.0150 | 23.1 | 64.5 |
| 1 | Ba | 650 | 6.6 | 0.0034 | 71.1 | 73.8 |
| 2 | BaBi | 650 | 11.7 | 0.0034 | 73.6 | 79.4 |
| 3 | $K_2$ | 600 | 6.9 | 0.0099 | 71.8 | 86.6 |
| 4 | BaBiSb | 600 | 2.9 | 0.0099 | 69.6 | 87.8 |
| 5 | $BaBiTe_{1.5}$ | 650 | 3.3 | 0.0099 | 79.1 | 91.1 |
| 6 | BaBiRe | 650 | 3.1 | 0.0105 | 75.0 | 88.2 |
| 7 | BaBiTl | 600 | 6.9 | 0.0099 | 69.0 | 89.6 |
| 8 | BaBiTh | 600 | 6.6 | 0.0105 | 66.1 | 84.2 |
| 9 | $BaBiTe_{1.5}V$ | 650 | 3.3 | 0.0099 | 77.8 | 89.8 |

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A catalyst composition comprising a catalyst having the following formula:

$Mo_aCu_bSn_cA_dL_eO_x$ wherein
A is selected form the group consisting of Li, Na, K, Cs, Mg, Ca, Sr, Ba, La, Ce, Th, U and mixtures thereof;
L is selected from the group consisting of Zn, Cd, Hg, Al, Ga, In, Tl, Ti, Zr, Hf, Nb, Ta, Ag, Au, Te, Se, Bi, Sb, Cr, As, S, Re, Mn, Ni, Co, Ru, Rh, Pd, Os, Ir, Pt and mixtures thereof; and
wherein
a is 0.1–15;
b is 0.1–15;
c is 0.05–12;
d is 0.01–10;
e is 0–12; and
x is the number of oxygens sufficient to satisfy the valence requirements of the other elements present.

2. The catalyst composition of claim 1 wherein A is selected from the group consisting of K, Cs, Ba, Mg, Ca and mixtures thereof.

3. The catalyst composition of claim 1 wherein A is Ba.

4. The catalyst composition of claim 1 wherein A is K.

5. The catalyst composition of claim 1 wherein L is selected from the group consisting of Bi, Te, Re and mixtures thereof.

6. The catalyst composition of claim 1 wherein:
a is 5;
b is 3–8;
c is 0.5–10; and
d is 0.5–10;
e is 0.5–6.

7. The catalyst composition of claim 1 wherein e is 0.

8. The catalyst composition of claim 1 wherein e is greater than 0.

9. The catalyst composition of claim 1 wherein the ratio of Mo/Cu/Sn/A is about 5/4/1/2-3.

* * * * *